United States Patent
Guagliano

(10) Patent No.: US 12,364,297 B1
(45) Date of Patent: Jul. 22, 2025

(54) SLEEVE ASSEMBLY

(71) Applicant: Vince Paul Guagliano, Rolling Hills Estates, CA (US)

(72) Inventor: Vince Paul Guagliano, Rolling Hills Estates, CA (US)

(73) Assignee: Vince Guagliano

( * ) Notice: Subject to any disclaimer, the term of this patent is extended or adjusted under 35 U.S.C. 154(b) by 697 days.

(21) Appl. No.: 17/475,038

(22) Filed: Sep. 14, 2021

Related U.S. Application Data

(60) Provisional application No. 63/079,884, filed on Sep. 17, 2020.

(51) Int. Cl.
| | | |
|---|---|---|
| *A41D 27/10* | (2006.01) | |
| *A61F 7/00* | (2006.01) | |
| *A61F 7/02* | (2006.01) | |
| *A61H 99/00* | (2006.01) | |

(52) U.S. Cl.
CPC .............. *A41D 27/10* (2013.01); *A61F 7/007* (2013.01); *A61H 99/00* (2013.01); *A41D 2400/322* (2013.01); *A61F 2007/008* (2013.01); *A61F 2007/0238* (2013.01); *A61H 2201/0207* (2013.01)

(58) Field of Classification Search
CPC ................. A41D 27/12; A41D 27/205; A41D 2400/322; A61F 7/007; A61F 2007/0029; A61F 2007/0034; A61F 2007/0071; A61F 2007/0072; A61F 2007/0078; A61F 2007/008; A61F 2007/0225; A61F 2007/023; A61F 2007/0233; A61F 2007/0234; A61F 2007/0236; A61F 2007/0238; A61H 99/00; A61H 2201/02; A61H 2201/0207; A61H 2201/0228; A61H 37/00; A61H 7/002–003; A61H 7/055; A61H 7/007; A61H 2201/16; A61H 1/0274–0288
See application file for complete search history.

(56) References Cited

U.S. PATENT DOCUMENTS

| | | | | |
|---|---|---|---|---|
| 2004/0260211 | A1* | 12/2004 | Maalouf | A61H 23/02 601/70 |
| 2020/0214369 | A1* | 7/2020 | Winningham | A41D 13/08 |

FOREIGN PATENT DOCUMENTS

| | | | | |
|---|---|---|---|---|
| CN | 106109084 | * | 11/2016 | |
| CN | 108030641 | * | 5/2018 | |
| KR | 200179508 | Y1 * | 4/2000 | |
| KR | 20190041247 | A * | 4/2019 | |
| TW | M425606 | U * | 4/2012 | |

* cited by examiner

*Primary Examiner* — Kendra D Carter
*Assistant Examiner* — Jaeick Jang

(57) ABSTRACT

A sleeve assembly is configured to provide heat therapy and massage therapy simultaneously. The sleeve assembly an outer sleeve operatively connected to an outer layer, a first pocket, and a second pocket. A rechargeable battery pack with controls is arranged in the second pocket through a second pocket opening. A heating element assembly is arranged within the first pocket through a first pocket opening attached to the rechargeable battery pack with controls with a cord. A user can wrap the outer sleeve around an arm to provide heat therapy and massage therapy to a client simultaneously.

5 Claims, 4 Drawing Sheets

SLEEVE ASSEMBLY

RELATED APPLICATION

This application claims priority to provisional patent application U.S. Ser. No. 63/079,884 filed on Sep. 17, 2020, the entire contents of which is herein incorporated by reference.

BACKGROUND

The embodiments herein relate generally to devices that use heat therapy.

Prior to embodiments of the disclosed invention heat therapy and massage therapy occurred separately. This was ineffective. Embodiments of the disclosed invention solve this problem.

A sleeve assembly is configured to provide heat therapy and massage therapy simultaneously. The sleeve assembly has an outer sleeve operatively connected to an outer layer, a first pocket, and a second pocket. A rechargeable battery pack with controls is arranged in the second pocket through a second pocket opening. A heating element assembly is arranged within the first pocket through a first pocket opening attached to the rechargeable battery pack with controls with a cord. A user can wrap the outer sleeve around an arm 42 to provide heat therapy and massage therapy to a client simultaneously.

In some embodiments, the rechargeable battery pack with controls further comprises an off down button arranged next to an on up button with a display therebetween.

In some embodiments, the heating element assembly further comprises a heating element, immediately adjacent to a silicone rubber layer. A felt layer is immediately adjacent to the silicone rubber layer and the first pocket.

In some embodiments, a remote control communicatively coupled to the rechargeable battery pack with controls. A capsule holds the rubber layer to the heating element and the felt layer. A third pocket, identical to the second pocket, can be arranged on an opposite side of the outer sleeve.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
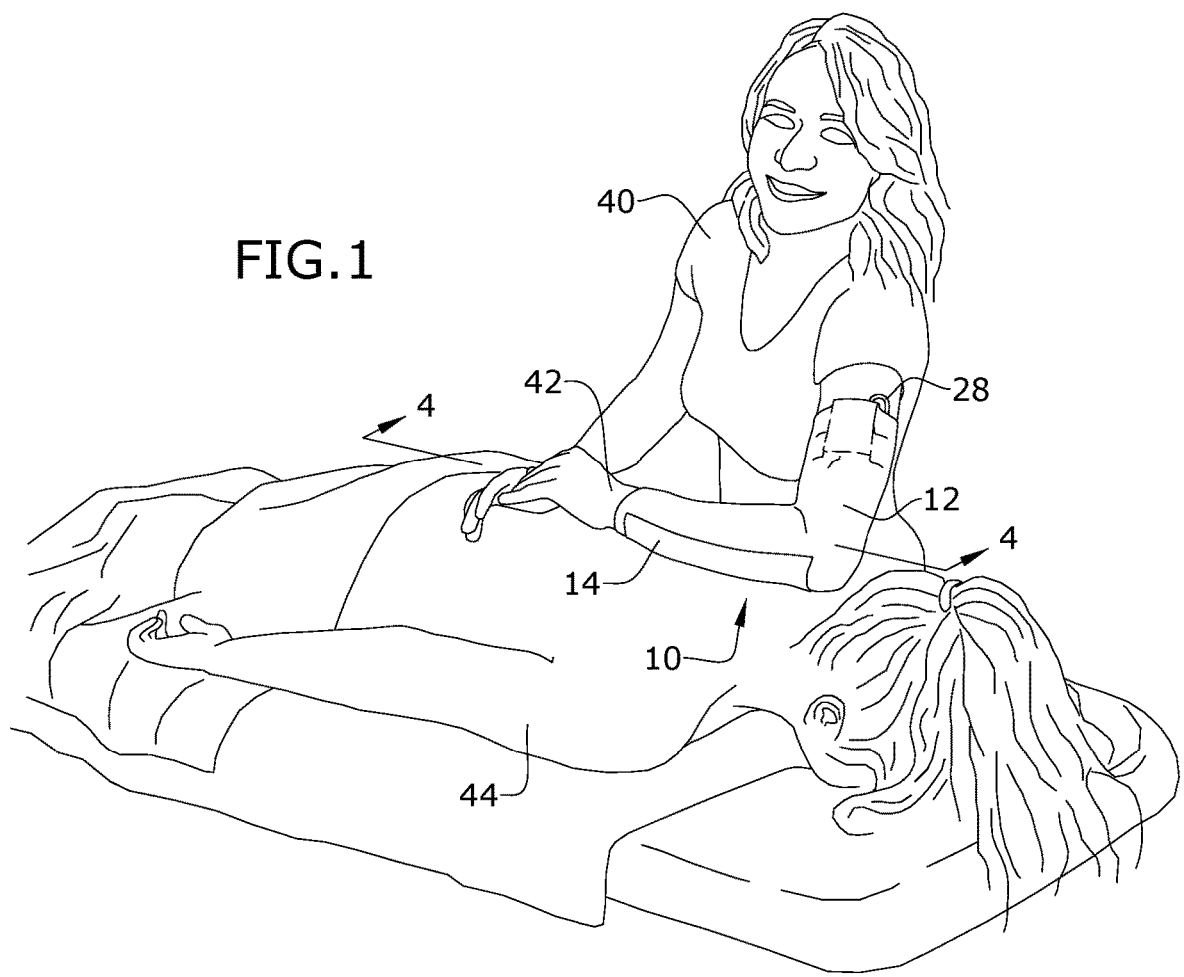
FIG. 1 shows a perspective view of one embodiment of the present invention shown in use.
Figure 2:
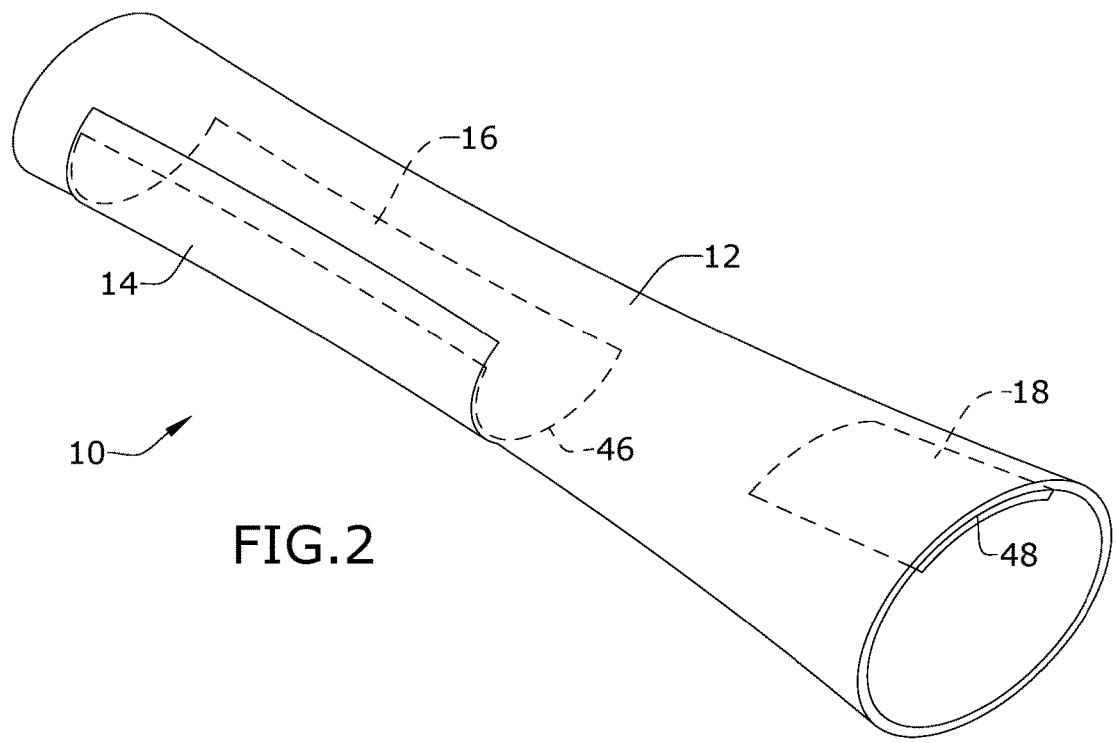
FIG. 2 shows a perspective view of one embodiment of the present invention.
Figure 3:
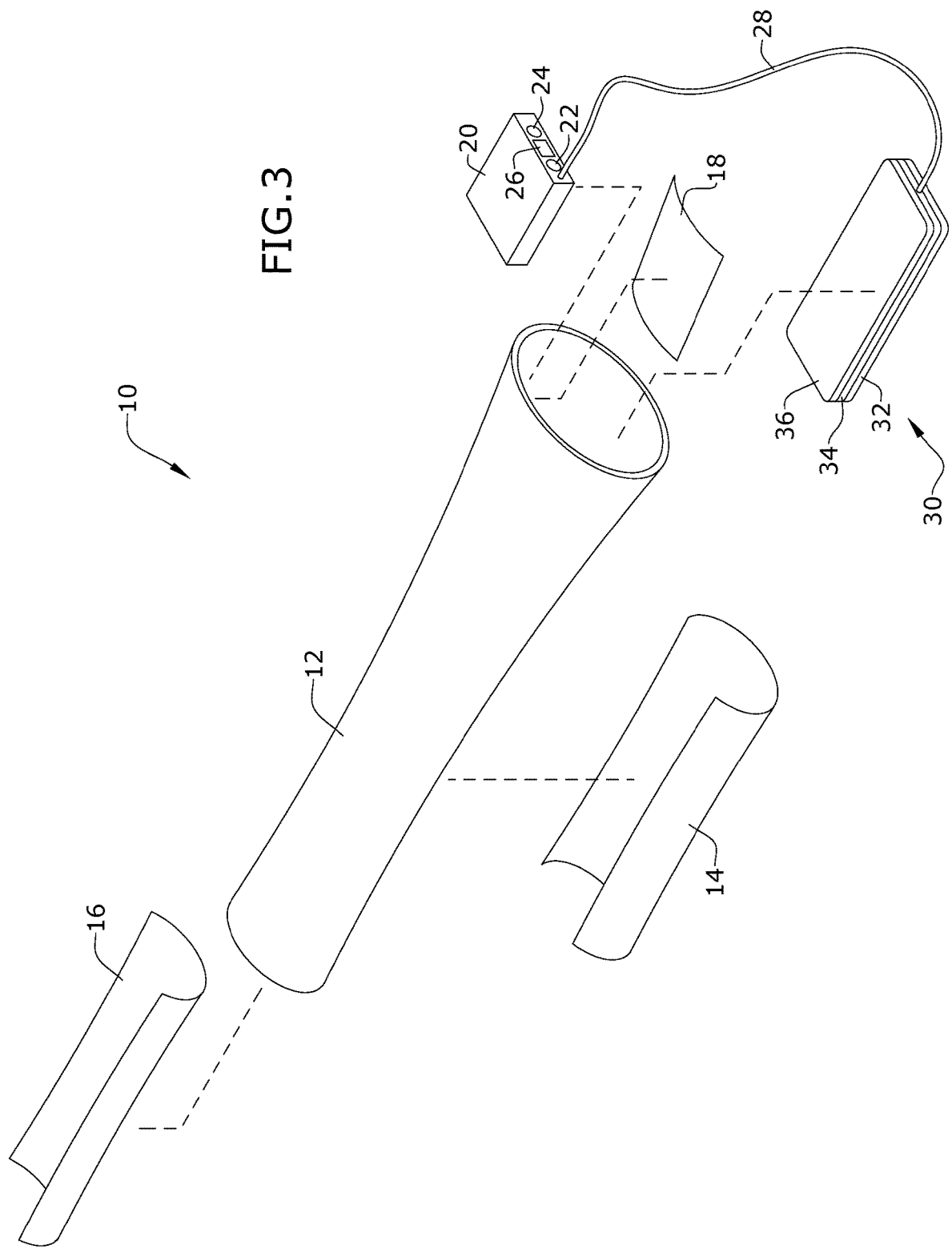
FIG. 3 shows an exploded view of one embodiment of the present invention.
Figure 4:
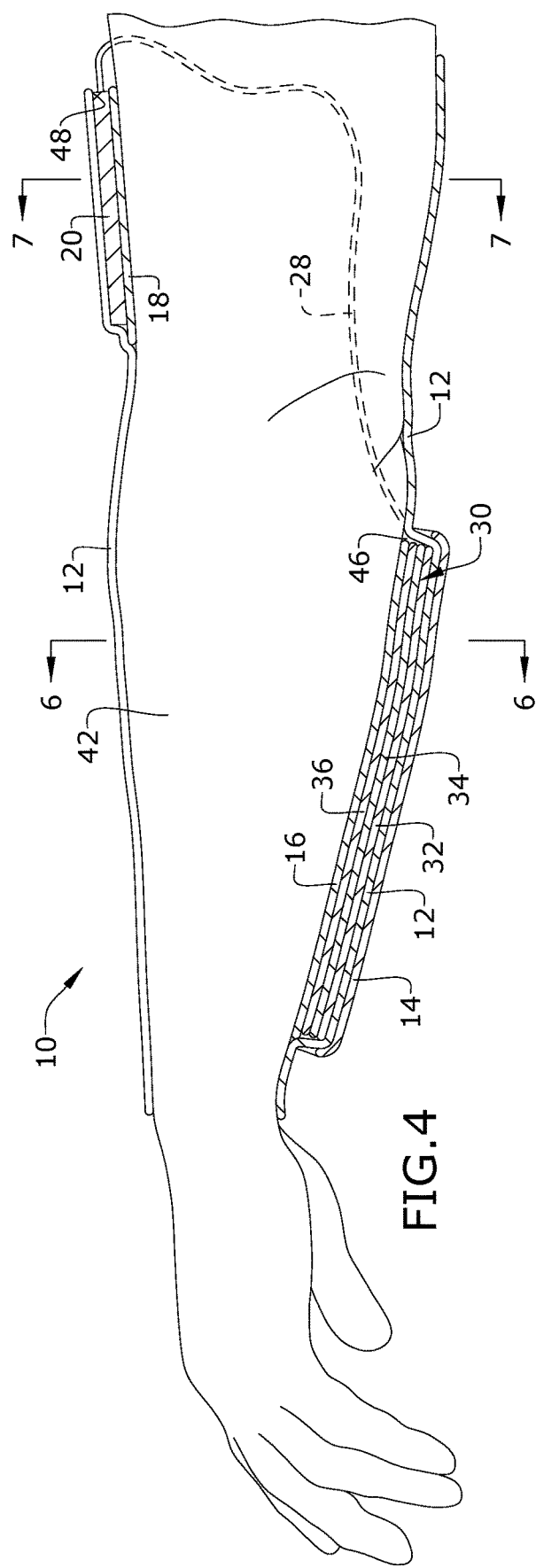
FIG. 4 shows a section view of one embodiment of the present invention taken along line 4-4 in FIG. 1.
Figure 5:
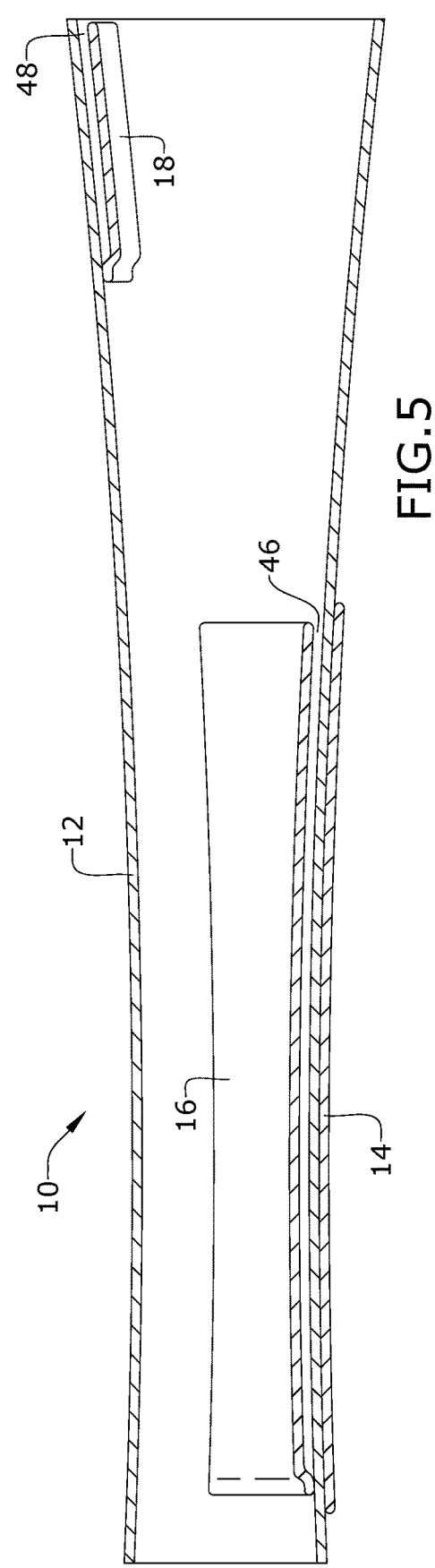
FIG. 5 shows a section view of one embodiment of the present invention.
Figure 6:
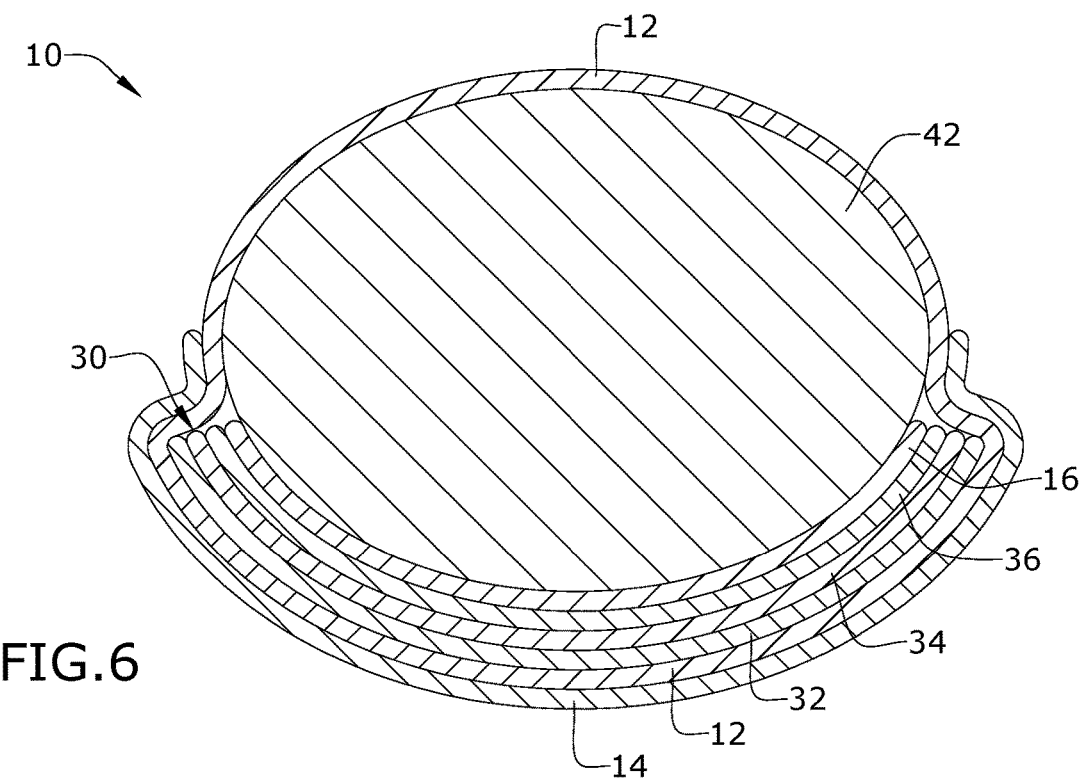
FIG. 6 shows a section view of one embodiment of the present invention taken along line 6-6 from FIG. 4.
Figure 7:
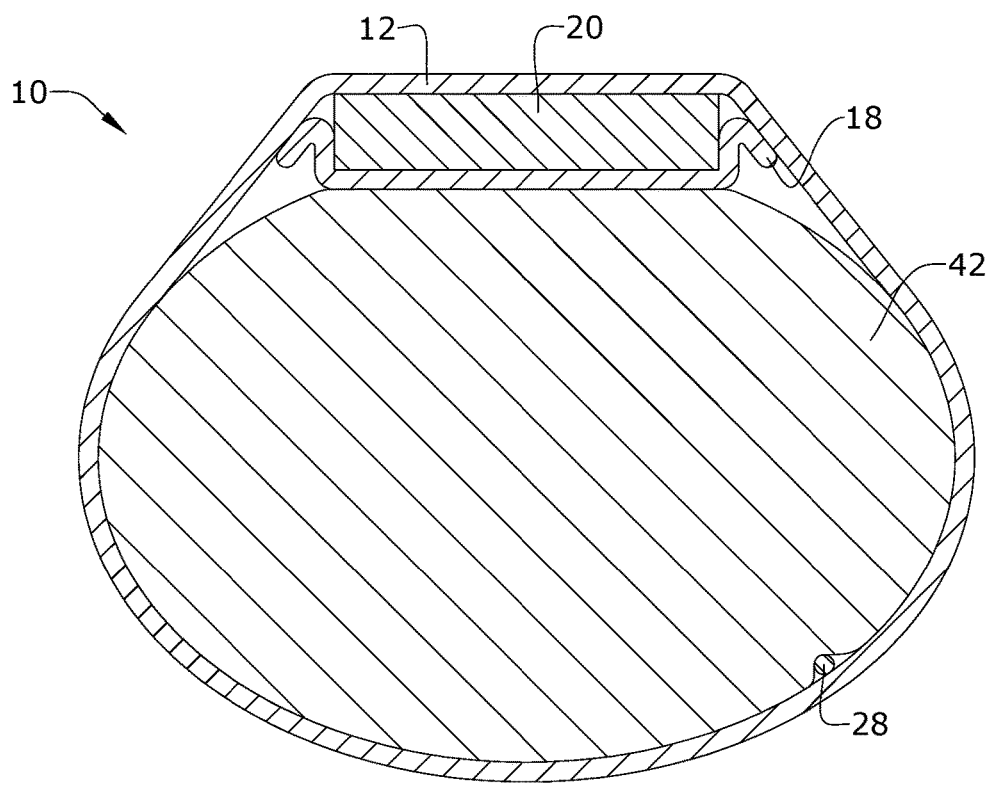
FIG. 7 shows a section view of one embodiment of the present invention taken along line 7-7 from FIG. 4.

By way of example, and referring to FIG. 1, one embodiment of a sleeve assembly 10 is configured to provide heat therapy and massage therapy simultaneously. The sleeve assembly 10 has an outer sleeve 12 operatively connected to an outer layer 14, a first pocket 16, and a second pocket 18. A rechargeable battery pack with controls 20 is arranged in the second pocket 18 through a second pocket opening 46. A heating element assembly 30 is arranged within the first pocket 16 through a first pocket opening 48 attached to the rechargeable battery pack with controls 20 with a cord 28. A user 40 can wrap the outer sleeve 12 around an arm 42 to provide heat therapy and massage therapy to a client 44 simultaneously.

In some embodiments, the rechargeable battery pack with controls 20 further comprises an off down button 22 arranged next to an on up button 24 with a display 26 therebetween.

In some embodiments, the heating element assembly 30 further comprises a heating element 32, immediately adjacent to a silicone rubber layer 34. A felt layer 36 is immediately adjacent to the silicone rubber layer 34 and the first pocket 16.

In some embodiments, a remote control can be communicatively coupled to the rechargeable battery pack with controls 20. A capsule can hold the rubber layer 34 to the heating element 32 and the felt layer 36. A third pocket, identical to the second pocket, can be arranged on an opposite side of the outer sleeve 14.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, 16. In particular, any use of "step of" in the claims is not intended to invoke the provision of 35 U.S.C. § 112, 16.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A sleeve assembly, configured to provide heat therapy and massage therapy simultaneously, the sleeve assembly comprising:
   an outer sleeve further comprising an inner surface and an outer surface; wherein the outer surface is operatively connected to an outer layer, and the inner surface is operatively connected to a first pocket and a second pocket;
   a rechargeable battery pack with controls, arranged in the second pocket through a second pocket opening;
   a heating element assembly, arranged within the first pocket through a first pocket opening attached to the rechargeable battery pack with controls with a cord; the heating element assembly further comprising:
      a heating element immediately adjacent to the inner surface;
      a silicone rubber layer further comprising a top surface and a bottom surface;
   wherein the bottom surface of the silicon rubber layer is immediately adjacent to the heating element and the top surface of the silicone rubber layer is immediately adjacent to a felt layer; wherein the felt layer further comprises a top surface; wherein the top surface of the felt layer is immediately adjacent to the first pocket;
      wherein the heating element assembly operates to facilitate heat transfer through the outer layer to a client while the silicone rubber layer, the felt layer, and the first pocket reduce heat transfer to a user;
   wherein the user can wrap the outer sleeve around an arm to provide heat therapy and massage therapy to the client simultaneously.

2. The sleeve assembly of claim 1, wherein the rechargeable battery pack with controls further comprises an off down button arranged next to an on up button with a display therebetween.

3. The sleeve assembly of claim 2, further comprising a remote control communicatively coupled to the rechargeable battery pack with controls.

4. The sleeve assembly of claim 3, further comprising a capsule holding the rubber layer to the heating element and the felt layer.

5. The sleeve assembly of claim 4, further comprising a third pocket identical to the second pocket but arranged on an opposite side of the outer sleeve.

* * * * *